US00PP32799P2

(12) United States Plant Patent
Weber

(10) Patent No.: US PP32,799 P2
(45) Date of Patent: Feb. 9, 2021

(54) RASPBERRY PLANT NAMED 'CRIMSON TREASURE'

(50) Latin Name: ***Rubus idaeas* L.**
Varietal Denomination: Crimson Treasure

(71) Applicant: CORNELL UNIVERSITY, Ithaca, NY (US)

(72) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/602,224

(22) Filed: Aug. 29, 2019

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./156, 203, 204
See application file for complete search history.

*Primary Examiner* — Susan McCormick Ewoldt
*Assistant Examiner* — Karen M Redden
(74) *Attorney, Agent, or Firm* — Troutman Pepper Hamilton Sanders LLP (Rochester)

(57) ABSTRACT

This invention relates to a new and distinct primocane bearing red raspberry plant designated as 'Crimson Treasure' primarily adapted to growing conditions of west central New York and other regions of similar climate. The new plant is primarily characterized by sturdy upright canes, conical fruit that is longer than broad, an extended mid-season to late season primocane production period, open display of fruit and intense red fruit color.

4 Drawing Sheets

This invention was made with government support under grant number NYG-632421 awarded by the USDA. The government has certain rights in the invention.

FIELD

The present invention relates to a new and distinct primocane bearing (fall bearing) red raspberry plant designated as 'Crimson Treasure'. The plant is botanically known as *Rubus idaeas* L. The new and distinct red raspberry originated from a hand-pollinated cross of the Cornell selection NY02-57 (unpatented) and the variety 'Rafzaqu' (U.S. Plant Pat. No. 19,512 P3).

BACKGROUND

The new and distinct red raspberry originated from a hand-pollinated cross of the Cornell selection NY02-57 (unpatented) and the variety 'Rafzaqu' (U.S. Plant Pat. No. 19,512 P3). This cross was made and the resulting seedling grown in Geneva, N.Y. The seedling was selected from a controlled breeding plot in 2012 and was designated NY12-30 for testing. The new plant was asexually propagated by root cuttings and tissue culture at Cornell AgriTech in Geneva, N.Y. This propagation has demonstrated that the combination of traits that characterize this plant are fixed and remain true to type through successive generations of asexual propagation.

SUMMARY

The new raspberry plant 'Crimson Treasure' is primarily adapted to the climate and growing conditions of west central New York and other regions of similar temperate climate. This climate allows for the development of sturdy primocanes that produce mature fruit starting in the mid-fall season in late August extending through mid-November. In Geneva, N.Y., vegetative bud break in the spring begins in early April. Floricane flower buds emerge in mid-to-late April, with flowers opening mid-to-late May. Primocane flowers emerge in mid-July, with flowers opening in late July. The mean primocane season harvest date begins in late August and ends in mid-November in Geneva, N.Y. The mean floricane season harvest date begins in late June and ends in early August in Geneva, N.Y. 'Crimson Treasure' is hardy to at least USDA hardiness zone 4. The plant's drought and heat tolerance is unknown. 'Crimson Treasure' benefits from the use of protective structures such as plastic hoop houses or high tunnels, which allow for optimal cane growth and the complete harvest of the fall crop when the risk of frost is prevalent. When allowed to produce a floricane crop in the following summer, yield is maximized with approximately equal yield and mean fruit weight in both seasons. The mean yield for the primocane crop in Geneva, N.Y. (rows at 2.4 m spacing center to center) is 12,600 kg/ha. Mean floricane yield is 12,900 at the same spacing. Fruit storage at 1° C. indicates a minimum of 12 days of shelf life when picked at early maturity. The fruit of this variety is primarily intended for fresh market consumption and should be harvested at early maturity for this use. When harvested at late maturity, it is suitable for processing. Shipping characteristics are unknown. This plant is fully self-fertile and is pollinated by the wind action and a multitude of insect pollinators and hummingbirds where present.

The following traits have been repeatedly observed and are determined to be unique characteristics of the new raspberry plant 'Crimson Treasure', which in combination distinguish this raspberry plant as a new and distinct plant:

1. Extended harvest on primocanes;
2. High yields, especially when double cropped;
3. Sturdy upright canes with multiple branches;

4. Bright, intense red, cone shaped fruit; and
5. Sparse, short spines on mature sections of the canes.

The new raspberry plant 'Crimson Treasure' differs from its parents by combining upright canes and branching habit of the maternal parent NY02-57 with the cone shaped, shiny red fruit of the paternal parent 'Rafzaqu'. NY02-57 produces medium sized, round fruit that is light red and moderately firm on highly branched canes. 'Rafzaqu' produces large cone shaped fruit on very tall canes with concentrated fruiting at the top of the primocane.

The new raspberry plant 'Crimson Treasure' is dissimilar to other primocane fruiting varieties currently grown in New York in that the new plant has a very extended primocane harvest season, produces fruit on medium height canes with multiple branches that are sturdy and upright, allowing the fruit to be displayed at the top of the canopy for easy harvest.

The new raspberry plant 'Crimson Treasure' is most similar in fruiting season and cane stature to the unpatented plant 'Heritage' which has sturdy upright primocanes that are heavily pigmented greyed-red with many stout spines. The fruiting season of the new raspberry plant 'Crimson Treasure' begins at a similar time to 'Heritage' and extends as much as 30 days longer into the late season when only late season varieties such as 'Crimson Giant' (U.S. Plant Pat. No. 23,375 P3) and 'Josephine' (U.S. Plant Pat. No. 12,173) had previously been productive. This is facilitated by the branching of the canes and high number of fruiting laterals. The canes of the new raspberry plant 'Crimson Treasure' are light yellow-green colored (Y-G 144B) with short, sparse, grayed-purple (G-P 185A) colored spines on the mature sections. The fruit of the new raspberry plant 'Crimson Treasure' are most similar in shape to the fruit of the primocane variety 'Caroline' (U.S. Plant Pat. No. 10,412), which has large, dark red fruit that tend to be dull and that are slightly broader than long. In contrast, the fruit of the new raspberry plant 'Crimson Treasure' are longer than the fruit of 'Caroline' and more conic in shape, are more glossy but with similar color at maturity. The canes of 'Caroline' are variably pigmented red purple to greyed yellow, with few short spines and a waxy coating.

In comparison to the similar varieties 'Caroline' and 'Heritage', the new raspberry plant 'Crimson Treasure' differs by the following combination of characteristics described in Table 1 below. Color terminology referred to herein is based on The Royal Horticultural Society Colour Chart (2001 edition).

TABLE 1

Comparison Chart of Plant and Fruit Characteristics

| Characteristic | 'Crimson Treasure' | 'Caroline' | 'Heritage' |
|---|---|---|---|
| 1. Mature primocane color | Yellow-green 144B | Red purple 59B Greyed-yellow 160A | Greyed-red 180B |
| 2. Fruit shape | Conical | Broad conical | Round |
| 3. Fruit length (mm) | 23 | 18 | 15 |
| 4. Fruit width (mm) | 20 | 19 | 14 |
| 5. Fruit length × width ratio | 1.1 | 0.9 | 1.1 |
| 6. Mean fruit weight | 3.1 g | 2.5 g | 1.9 g |
| 7. Maximum fruit weight | 6.4 | 3.8 | 3.0 |
| 8. Mature fruit color | Red 45A | Red 45A | Red 53A |
| 9. Canes per plant | 24 | 31 | 29 |
| 10. Fruiting laterals per primocane | 18 | 14 | 18 |
| 11. Leaflet number | Primarily 5, sometimes 3 or mixed | 5 | Primarily 3 with up to 10% 5 |

BRIEF DESCRIPTIONS OF THE DRAWINGS

The accompanying color photographs illustrate typical characteristics of the new raspberry plant 'Crimson Treasure' and are as true to color as reasonably possible with photographic reproductions of this type. Color in the photographs may differ slightly from the color value cited in the detailed botanical description, which accurately describes the color of 'Crimson Treasure'. The photographs of canes and fruit were taken in Geneva, New York in the second year of harvesting fruit.

FIGS. 1A-C show typical fruit shape and size of the new raspberry plant 'Crimson Treasure' in a container (FIG. 1A), from a side view (FIG. 1B); and from a bottom view showing the cavity (FIG. 1C).

FIGS. 2A-C show typical primocane pigmentation and spine density of mature canes for the new raspberry plant 'Crimson Treasure' (FIG. 2A), for 'Caroline' (FIG. 2B), and for 'Heritage' (FIG. 2C).

DETAILED BOTANICAL DESCRIPTION

The photographs in the accompanying colored drawings together with the descriptions of the new raspberry plant 'Crimson Treasure' herein are based upon observations taken during the 2017-19 growing seasons in Geneva, N.Y., on plants that were approximately 14 to 18 months old. Measurements were taken on plants grown in a perennial planting in a high tunnel system that was planted in Geneva, N.Y. in 2016 with the canes emerging naturally in late April each year. Flower measurements and characteristics were taken from secondary flowers and fruit measurements from secondary fruit. Mean measurements of fruit size were taken on 10 fruit samples throughout the season. Measurements of flower and fruit parts are means of 10 fruit samples. Cane measurements were taken within the center third of the cane unless otherwise noted.

Classification:

*Family*.—Rosaceae.

*Botanical*.—*Rubus idaeus* L.

*Common name*.—Red Raspberry.

Parentage: NY02-57 (unpatented) x 'Rafzaqu' (U.S. Plant Pat. No. 19,512 P3).

Plant: Upright and branched growth habit. Plant mean height is 132 cm. Plant mean width is 99 cm.

Primocanes:

*Primocane color*.—Yellow-green 144B. Floricane color: greyed-orange N172D.

Figure 1A:
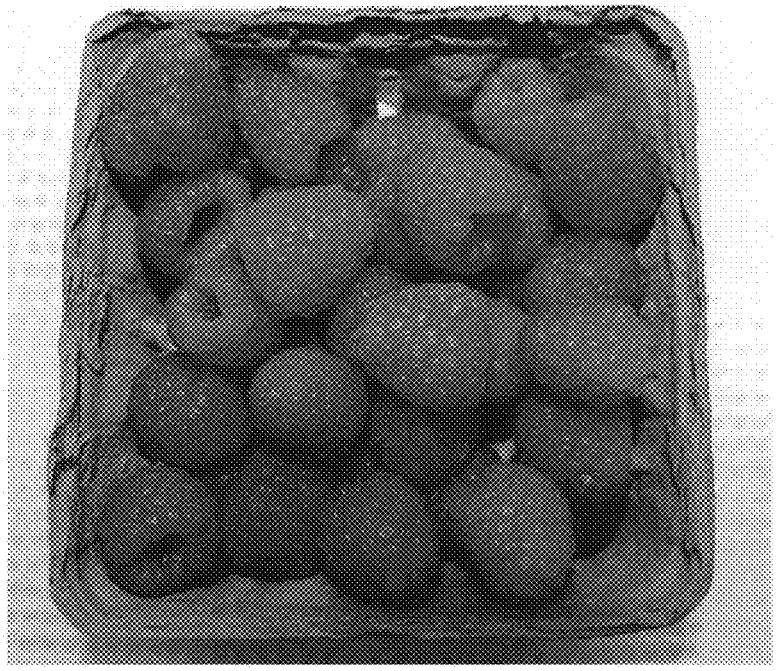
Figure 1B:
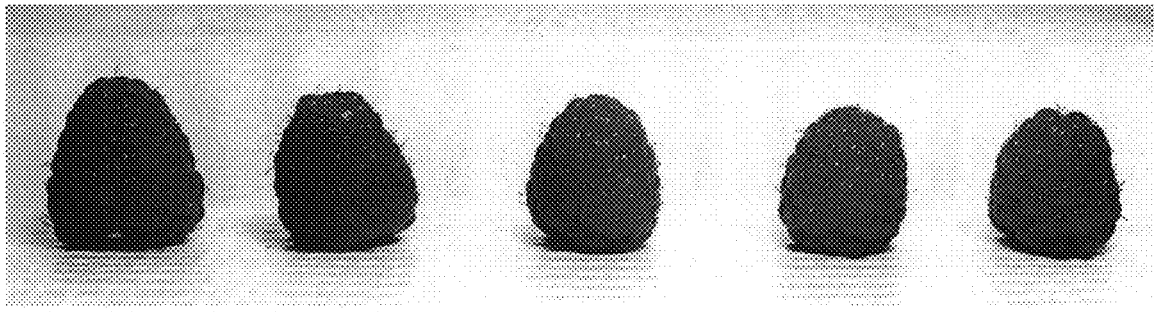
Figure 1C:
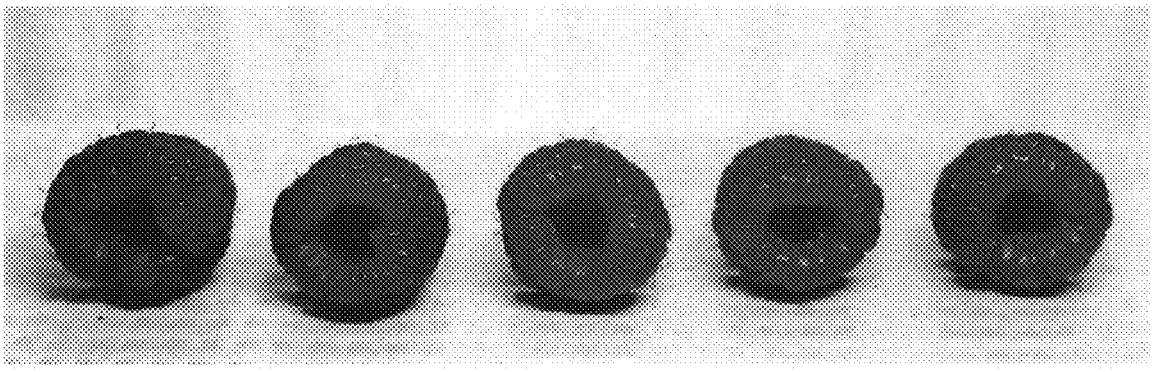
Figure 2A:
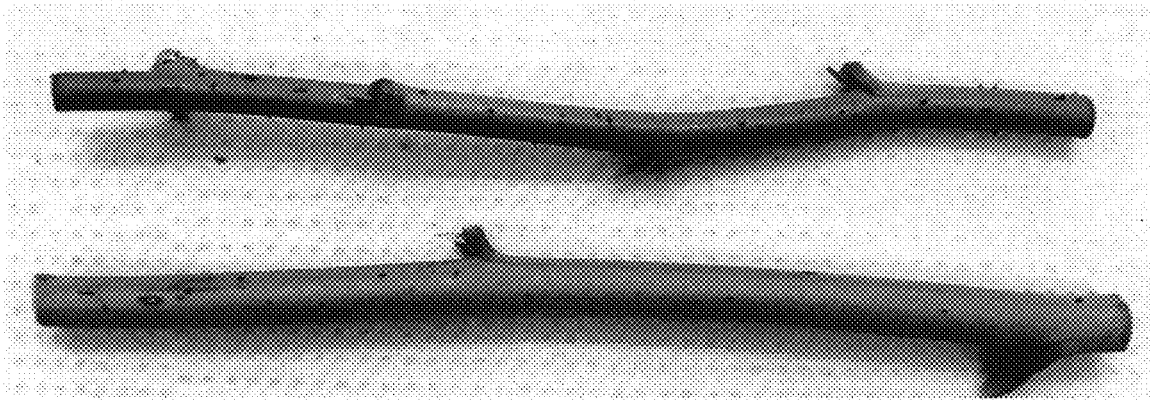
Figure 2B:
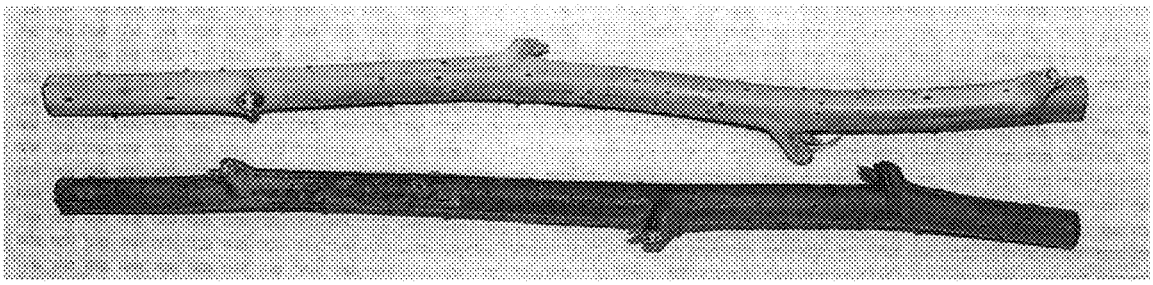
Figure 2C:
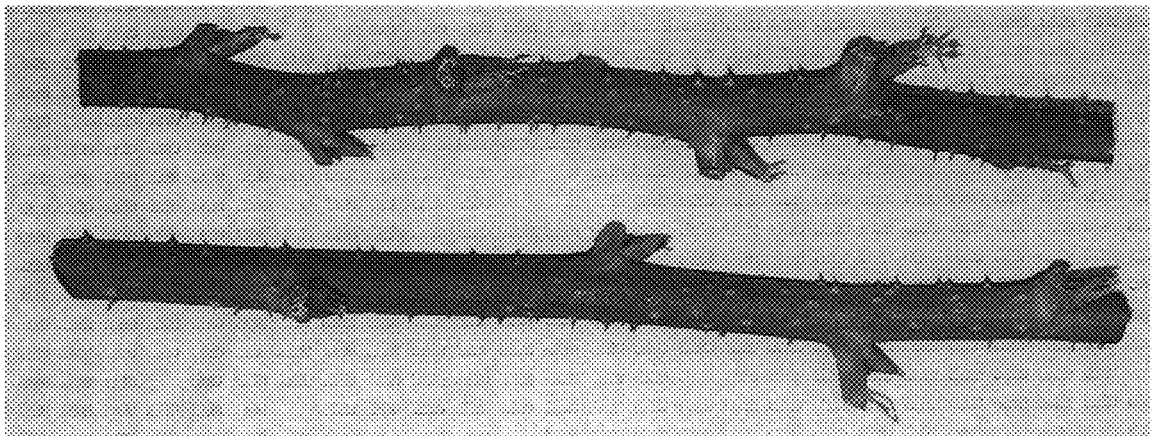
Figure 3:
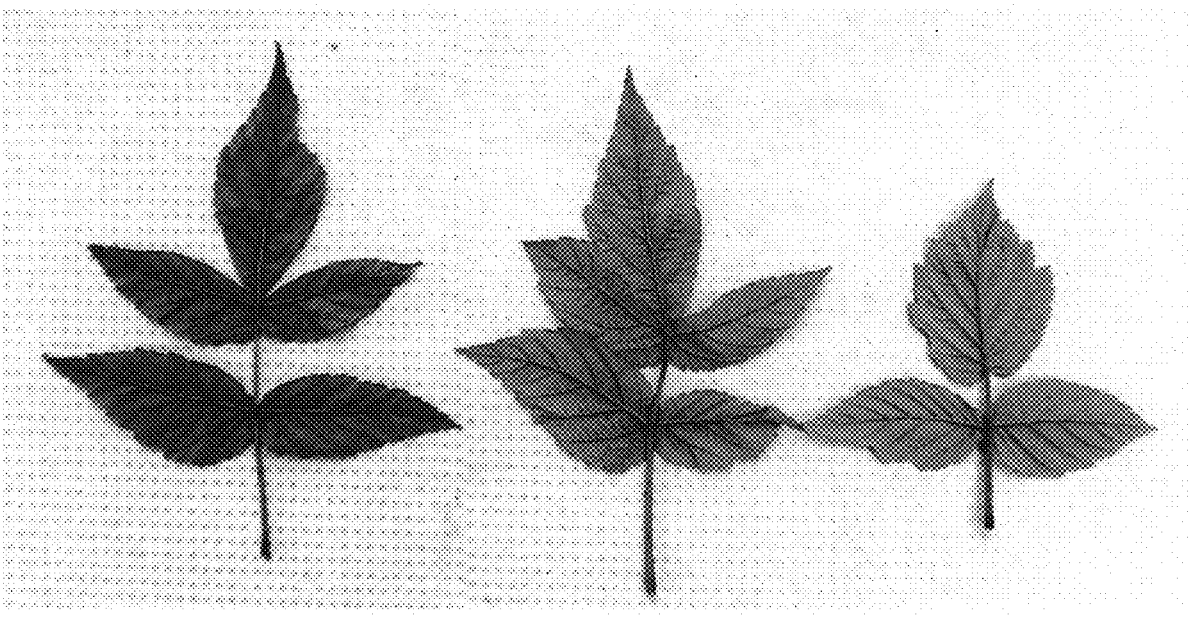
FIG. 3 shows mature leaves having different leaflet arrangements found on the new raspberry plant 'Crimson Treasure', including 5 leaflets; mixed with fused middle and terminal leaflet; and 3 leaflets (from left to right, respectively).
Figure 4:
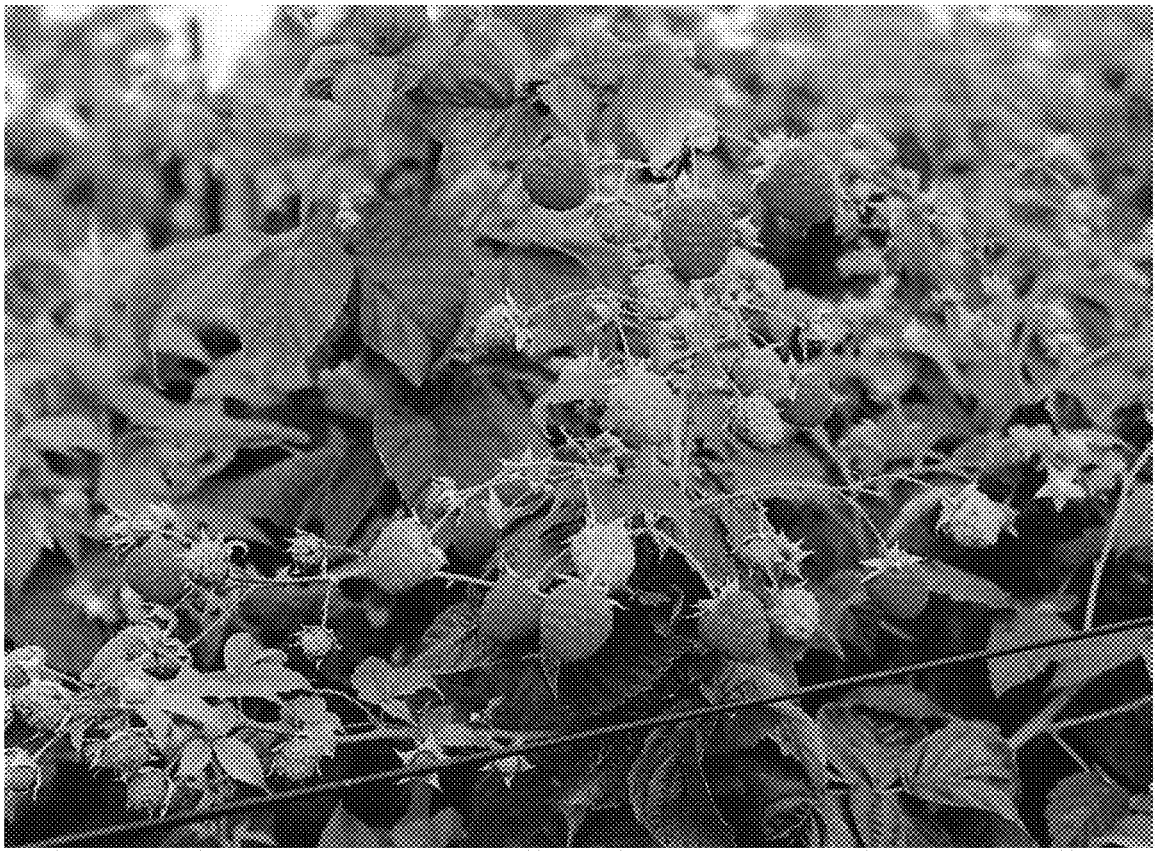
FIG. 4 shows the fruiting habit of the new raspberry plant 'Crimson Treasure' showing open display of fruit on a branched cane.

*Cane texture*.—Sparse to moderate prickle density uniform along the developing primocane with a smooth epidermis between spines (as displayed in FIG. 2A).
*Cane length*.—1.2 m-1.5 m; mean 1.3 m.
*Cane diameter*.—7-10 mm; mean 8 mm.
*Number of fruiting lateral branches*.—13-22; mean 18.
*Maximum fruiting lateral length*.—46 cm.
*Cane pubescence*.—None.

Spines:
*Density*.—Moderate at base, low at middle third.
*Form*.—Stout.
*Length*.—Mean 2 mm.
*Apex*.—Curved downward.
*Color*.—Greyed-purple 185A on mature canes.

Leaves:
*Leaf type*.—Compound with opposite leaflet arrangement and a single terminal leaflet; typically 5 leaflets; approximately 15%, 3 leaflets; secondary leaflet(s) fused with terminal leaflet common. Pinnate leaf venation. Vein color is yellow-green 144C as viewed from the underside surface.
*Mature leaflet color*.—Upper surface Green 137A; lower surface Green N138C.
*Leaf arrangement*.—Alternate with 1 leaf per node.
*Terminal leaflet length*.—7.9-13.2 cm; mean 9.9 cm.
*Terminal leaflet width*.—4.3-7.9 cm; mean 6.0 cm.
*Terminal leaflet length to width ratio*.—1.6.
*Basal leaflet length*.—6.9-11.5 cm; mean 8.6 cm.
*Basal leaflet width*.—3.9-7.0 cm; mean 5.1 cm.
*Basal leaflet length to width ratio*.—1.7.
*Leaflet shape*.—Ovate. Leaflet texture: Rugose.
*Terminal leaflet tip*.—Acuminate.
*Basal leaflet attachment*.—Cuspidate.
*Leaflet margins*.—Doubly serrate.
*Terminal leaflet number of serrations*.—102 mean.
*Basal leaf attachment*.—Cordate to auriculate.
*Leaflet overlap*.—None.
*Petiole length*.—4.6 cm.
*Petiole width*.—2.3 mm.
*Petiole spines*.—Present, sparse.
*Petiole spine apex*.—Slight curve downward toward stem.
*Petiole color*.—Yellow-green 144B.

Stipules:
*Quantity per leaf*.—2.
*Shape*.—Straight and erect.
*Length*.—3-8 mm; mean 5.5 mm.
*Color*.—Yellow-green 144B.

Flowers:
*Diameter*.—1.8-2.2 cm; mean 2.1 cm.
*Bud*.—Flower buds are uniform round, tapering to a point (i.e., conical). Mean diameter of mature primary flower buds is 6.25 mm across the base. Secondary and lower tier buds are smaller. The color of the flower buds is yellow-green 144D. The seams between the sepals are lighter color, similar to green 142D.
*Fragrance*.—Absent.
*Petals number*.—Typically 5, occasionally 6 or 7 in primary flowers.
*Petal shape*.—Obovate.
*Petal length*.—4-6 mm; mean 5.1 mm.
*Petal width*.—2-3 mm; mean 2.3 mm.
*Petal length to width ratio*.—2.3.
*Petal color*.—White 155C. Petal margins are entire. The texture is smooth with slightly concave cupping to the inside of the flower. The surface color is the same on the top and the bottom surfaces, 155C. Mean number of flowers per panicle is 10.7. Mean pedicle length is 16 mm. The pedicle color is yellow-green 144D. Mean peduncle length on primocanes is 13.2 cm. Mean peduncle length on floricanes is 19.7 cm. The mean diameter of the peduncle is 3 mm mid-way between the attachment and the tip. The mean peduncle diameter at the attachment point is 5.5 mm. The peduncle color is yellow-green 144B, with light blush of greyed-purple 184D.
*Sepal number*.—Typically 5; often 6 or 7 in primary flowers. Sepals have a pubescent texture with small prickles present.
*Sepal length*.—7-9 mm; mean 7.5 mm.
*Sepal color*.—Upper surface Yellow-green 144D; lower surface Yellow-green 144A.
*Mean stigma number*.—93.
*Stigma color*.—White 155B.
*Mean stamen number*.—80.
*Anther color*.—White 155A.
*Anther filament color*.—White 155D.
*Stamen height*.—Below stigmatic surface.

Fruit:
*Shape*.—Broad conic. The mean cavity diameter is 8 mm, and the mean depth of the cavity is 13.8 mm.
*Fruit length*.—2.0-2.8 cm; mean 2.3 cm.
*Fruit width*.—1.6-2.2 cm; mean 1.9 cm.
*Fruit length to width ratio*.—1.1.
*Weight*.—1.6-6.4 g; mean 3.1 g.
*Number of drupelets*.—128 for mean fruit size.
*Color of mature fruit*.—Red group 45A. Color of fruit flesh: 45A.
*Pedicel diameter*.—1 mm.
*Pedicel spines*.—Present; numerous; curved back towards cane.
*Adherence to receptacle*.—Low.

What is claimed:

1. A new and distinct cultivar of raspberry plant named 'Crimson Treasure' as herein described and illustrated by the characteristics set forth above.

* * * * *